Figure 1:
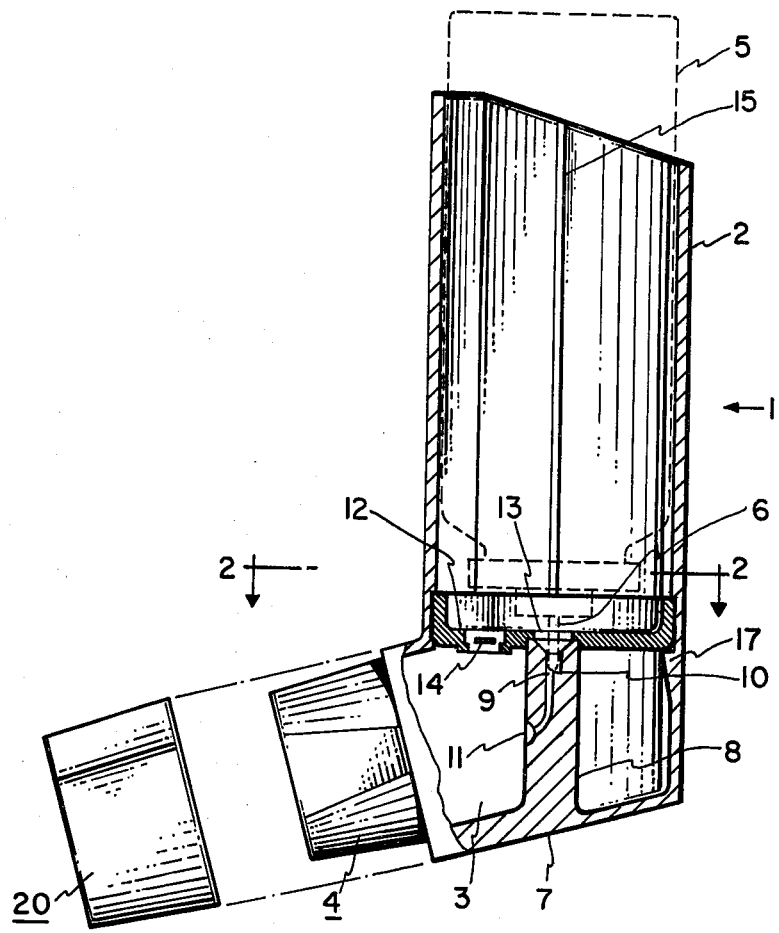

United States Patent [19]

Kistler

[11] 4,291,688
[45] Sep. 29, 1981

[54] INHALATION DEVICE

[75] Inventor: Frederic E. Kistler, Horw, Switzerland

[73] Assignee: Schering Corp., Kenilworth, N.J.

[21] Appl. No.: 104,610

[22] Filed: Dec. 17, 1979

[30] Foreign Application Priority Data

Jan. 11, 1979 [EP] European Pat. Off. ........ 79810001.2
Oct. 25, 1979 [EP] European Pat. Off. ........ 79810138.2

[51] Int. Cl.³ .......................................... A61M 15/00
[52] U.S. Cl. ............................................. 128/200.23
[58] Field of Search ...................... 128/200.23, 200.14, 128/200.18, 203.15

[56] References Cited

U.S. PATENT DOCUMENTS

| | | | |
|---|---|---|---|
| 3,012,555 | 12/1961 | Meshberg | 128/200.23 |
| 3,404,681 | 10/1968 | Fowler | 128/200.23 |
| 3,456,646 | 7/1969 | Phillips et al. | 128/200.23 |
| 3,506,004 | 4/1970 | Mann et al. | 128/200.23 |
| 3,647,115 | 3/1972 | McCann et al. | 222/39 |
| 3,732,864 | 5/1973 | Thompson et al. | 128/200.23 |
| 3,789,843 | 2/1974 | Armstrong et al. | 128/200.23 |
| 3,814,297 | 6/1974 | Warren | 128/200.23 |
| 3,826,413 | 7/1974 | Warren | 128/200.23 |
| 3,837,341 | 9/1974 | Bell | 128/203.15 |

FOREIGN PATENT DOCUMENTS 2803993 8/1978 Fed. Rep. of Germany ....................... 128/200.23

OTHER PUBLICATIONS

McGavin, "A Modified Aerosol Inhaler for Teaching Technique", *The Lancet*, Dec. 4, 1976.

*Primary Examiner*—Henry J. Recla
*Attorney, Agent, or Firm*—Vincent H. Gifford; Bruce M. Eisen

[57] ABSTRACT

An inhalation device of the type adapted to receive and locate an aerosol container designed to administer a multiplicity of metered doses, said aerosol container having a composition under pressure therein and having metering valve means including a valve stem and associated metering means, the valve stem having an axial discharge tube extending therethrough for discharge of a metered dose upon actuation of said metering valve means by depression of said valve stem, said inhalation device comprising a body having a skirt adapted to receive and locate said aerosol container in a first end thereof and a head-piece connected to a second end of said skirt, a mouth-piece extending from said head-piece and in communication therewith, and an audible signal generating means, said head-piece having actuating means for said metering valve means and a discharge passageway leading to a discharge orifice directed towards said mouth-piece, said actuating means being engageable with the valve stem upon location of the container within the skirt and operable to actuate the metering valve means whereby a metered dose is discharged through the valve stem discharge tube and the discharge passageway and discharge orifice into the mouth-piece, wherein said audible signal generating means is located in said air-passageway within the body upstream of said discharge orifice and surrounds the actuating means for the metering valve means, and is actuatable upon inhalation through said mouth-piece when said inhalation device is in engagement with said container.

15 Claims, 5 Drawing Figures

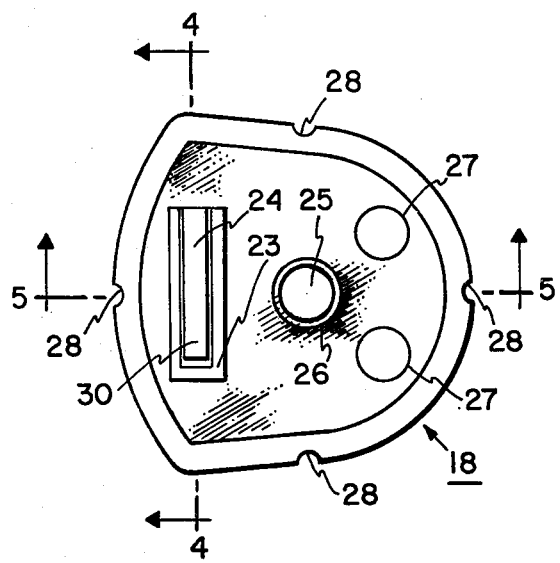
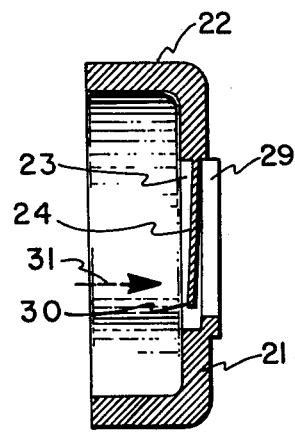
FIG.3    FIG.4
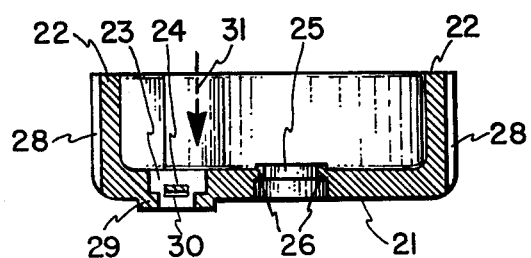
FIG.5

INHALATION DEVICE

This invention relates to improvements in inhalation devices for aerosol products contained in multi-dose aerosol containers and in particular to an inhalation device especially suited for the oral administration, by inhalation, of medicaments such as bronchodilators and corticosteroids.

On inhalation, these medicaments must reach the smallest bronchial tubes in the lungs to get into contact with the endothelial lining, where their medicinal effect is needed for example in the treatment of patients suffering from obstructive bronchitis or asthma. However, many patients on long-term inhalation therapy find it difficult to use inhalation devices for medicaments correctly, and consequently do not obtain full benefit from the medicament. Ideally, the patient should exhale as far as possible, hold the mouthpiece of the inhalation device between his teeth, close his lips and inhale as deeply as possible through the mouth, and, while inhaling, actuate the aerosol container within the inhalation device in order to obtain a metered dose of medicament. If the patient correctly carries out this procedure, the medicament is carried down into the bronchial tubes of the lungs where its therapeutic effect is needed. Unfortunately, many patients find it difficult to synchronise actuating the aerosol container and inhaling the medicament expelled therefrom; they may not inhale sufficiently or even not inhale at all. The result is that the active substance is not inhaled into the lungs but lodges in the mouth or throat instead, where it is ineffective for the treatment of asthma or obstructive bronchitis.

It has therefore been proposed ("The Lancet", Dec. 4, 1976) to modify the inhalation device by attaching a whistle or siren to the outside and by blocking any air-spaces between the aerosol container and the adjacent part of the housing of the inhalation device. When th patient correctly uses this modified device, the whistle or siren sounds as the air passes through it, and the resulting audible signal indicates to the patient that he should press the container in order to receive the metered dose.

This modified device unfortunately suffers from a number of disadvantages: it is not simple to manufacture; it is too bulky; and the externally attached whistle or siren can get damaged or become separated (e.g. get broken off) if the inhalation device (with its aerosol container) is simply carried in the pocket or a case along with other articles.

It is therefore an object of the present invention to provide an improved inhalation device that generates an audible signal on correct inhalation, and in particular an improved inhalation device that avoids or mitigates the aforesaid disadvantages by having its audible signal generating means in a position where it cannot be separated or damaged in normal use, by being simple and cheap to manufacture, and by being no more bulky than the standard known inhalation device. Furthermore, this improved inhalation device enables the continued use of known inhalation devices without structural modification, in that the audible signal generating means is manufactured separately and is simply inserted into a known device.

Accordingly, the invention provides an inhalation device of the type adapted to receive and locate an aerosol container designed to administer a multiplicity of metered doses, said aerosol container having a composition under pressure therein and having metering valve means including a valve stem and associated metering means, the valve stem having an axial discharge tube extending therethrough for discharge of a metered dose upon actuation of said metering valve means by depression of said valve stem, said inhalation device comprising a body having a skirt adapted to receive and locate said aerosol container and a head-piece, a mouth-piece extending from said head-piece and in communication therewith, an air-passageway extending through at least part of said body to said mouth-piece and providing a path for air to flow into the mouth-piece upon inhalation through the mouth-piece, and an audible signal generating means, said head-piece having actuating means for said metering valve means and a discharge passageway leading to a discharge orifice, said actuating means being engageable with the valve stem upon location of the container within the skirt and operable to actuate the metering valve means whereby a metered dose is discharged through the valve stem discharge tube and the discharge passageway and discharge orifice into the mouth-piece, wherein said audible signal generating means is located in said air-passageway within the body upstream of said discharge orifice and surrounds the actuating means for the metering valve means and/or the metering valve means itself, and is actuatable upon inhalation through said mouth-piece when said inhalation device is in engagement with said container.

As the audible signal generating means is located in the space surrounding the actuating means for the metering valve means and/or surrounding the metering valve means itself, it cannot be separated or damaged in normal use. Furthermore, it does not add to the bulk of the inhalation device.

The actuating means for said metering valve means is preferably a valve stem boss adapted to receive the valve stem within a discharge passageway therein, said discharge passageway having means for limiting entry therein of said valve stem and a discharge orifice communicating with said discharge passgeway and adapted to discharge said metered dose through said mouth-piece.

Although the valve stem boss is designed to grip the valve stem of the container, the container is relatively easily dislodged (e.g. if the inhalation device is carried loose in the pocket or a case with other articles) unless the skirt is long enough to accommodate and protect the container. The skirt therefore should not simply overlap the top part of the container but extend at least half way, preferably at least three quarters of the way, along the container, and thus accommodate the container and hold it snugly inside.

The audible signal generating means (for convenience hereinafter referred to as "sounding device") is located preferably inside the head-piece or the adjacent part of the skirt where it will not interfere with the movement of the container necessary to actuate the valve and discharge the metered dose. A convenient position is upstream of the boss in the space between the container (when present) and the valve stem boss; in particular the sounding device can be placed adjacent to and most preferably abutting against the valve stem boss, near the junction of the head-piece and skirt. The part of the sounding device that abuts against the valve stem boss can be recessed for better support.

Although a variety of sounding devices are known in the art, the sounding device that is chosen should be small enough to fit inside the inhalation device as described above, e.g. between the space reserved for the container and the valve stem boss. Moreover the sounding device is preferably a "one-way" sounding device, i.e. it should provide an audible signal only on adequate inhalation and not on exhalation. The preferred sounding device is therefore a membrane or membrane-like element having a vibratory reed or tongue therein; the one-way sounding effect can be provided by giving the reed or tongue a small angular displacement against the air-flow resulting on inhalation. Such a sounding device can be manufactured separately from the inhalation device and indeed designed so that commerically available inhalation devices can be used without modification; the sounding device is merely inserted. Thus it is preferred to have the membrane or membrane-like element inside the body near the junction of the head-piece and skirt in a plane substantially perpendicular to the air-path and in particular abutting against the valve stem boss. In this position, the membrane or membrane-like element surrounds the valve stem and optionally the valve stem boss and thus substantially blocks the air path, so that air flow is directed past the reed or tongue on inhalation.

A sounding device based on a vibratory reed or tongue is cheap and simple to produce; for example, it can be stamped out of sheet metal or be manufactured by injection-moulding. It can easily be inserted into and retained in the inhalation device, and does not hinder the normal use of the inhalation device. Moreover, because it fits inside the inhalation device, it does not add to the bulk of the inhalation device and is not subject to damage in normal use. The membrane-like element preferably carries at least one extending piece designed to rest against the walls of the skirt and thus hold it in place.

In order to provide an air path through the body to the mouth-piece, a small hole can be left opposite the mouth-piece near the junction of the skirt and head-piece, and the sounding device can be located between this hole and the mouth-piece. However, preferably one or more channels are provided between the container and the skirt as a path for air to pass into the head-piece and then out of the mouth-piece on inhalaton.

Figure 2:
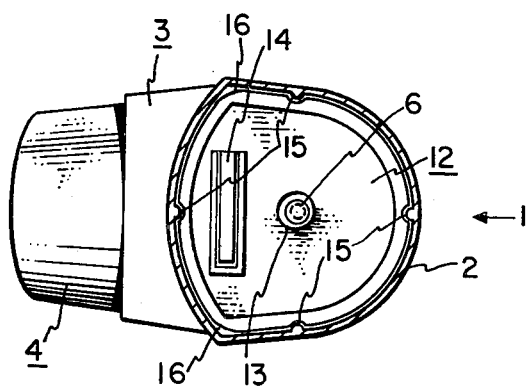

Particularly preferred embodiments of the invention will now be described with reference to the accompanying drawings in which:

FIG. 1 is a side elevational view of a preferred form of inhalation device, partly in section, FIG. 2 is an enlarged sectional view of the inhalation device taken along line 2—2 of FIG. 1, FIG. 3 is a plan view of an especially preferred form of sounding device according to the invention, and FIGS. 4 and 5 respectively are sections on the lines 4—4 and 5—5 of FIG. 3. (All these figures are not necessarily to scale).

The inhalation device 1, which is preferably made of rigid or semi-rigid plastic material, comprises a skirt 2 and a head-piece 3, together constituting a body, and a mouth-piece 4. The skirt 2 is designed to receive an aerosol container 5 of standard type, which upon depression of a valve stem 6 dispenses metered doses of medicament through an axial discharge tube therein. In FIG. 1, the container 5 is indicated by broken lines, since its presence is not necessary to the general description of the invention but only to how the invention is used. The head-piece 3 of the inhalation device 1 has a top portion 7 from which a valve stem boss 8 depends. Valve stem boss 8 is adapted to receive and grip valve stem 6 of container 5 by means of a longitudinal discharge passageway 9 therein. This discharge passageway 9 has one or more abutments 10 therein designed to limit the penetration of the valve stem 6 into the boss 8 when pressure is exerted on the opposite end of the container 5. The discharge passageway 9 communicates with a discharge orifice 11 substantially on the longitudinal axis of the mouth-piece 4. The mouth-piece 4 can be closed by a cap 20 when the inhalation device 1 is not being used. The inhalation device 1 contains a thin membrane 12 abutting against the boss 8 and surrounding the valve stem 6. This membrane 12, which is shown in elevation in FIG. 2, has an aperture 13 at its center to receive the valve stem 6, and in particular has a U-shaped or rectangular reed or tongue 14 stamped in it. The reed or tongue 14 is preferably set at a small angle to the plane of the membrane 12 and bent towards the container 5, so that it will vibrate only when the air flows first past the membrane 12 and then out through the mouth-piece 4, as in inhalation. This provides a "one-way" sounding device.

The skirt 2 of the inhalation device 1 preferably has small ribs 15 protruding therefrom inside, these having the dual function of strengthening the skirt 2 and limiting the side-ways movement of the container 5. The membrane 12 is correspondingly notched to accommodate these ribs 15. Normally the membrane 12 will reside comfortably inside the inhalation device 1 without further support, but if desired a number of abutments 17 can be provided in the head-piece 3 of the inhalation device 1, e.g. as continuations of the ribs 15. The membrane 12 fits snugly inside the skirt 2 but has sufficient air gaps around it or through it to allow good inhalation by the patient; small gaps, as at 16, are sufficient. If necessary, a small aperture or a number of small apertures may be made in the membrane 12. However, the air gaps in or around the membrane must be sufficiently constricted to force an air flow past the reed or tongue 14 during inhalation and thus activate it. The container 5 is circular in cross-section, so an air path is provided between the container 5 and the skirt 2 in the direction of the air gaps 16, and this extends past the membrane 12 and through the head-piece 3 and mouth-piece 4.

The membrane 12 should be sufficiently rigid to allow insertion into the inhalation device 1 without suffering deformation. It can be made of a readily available cheap metal that can be readily stamped to the desired form, e.g. a moderately hard metal such as hard or semi-hard brass. Brass sheet 0.1 to 0.2 mm. thick is very suitable. Reed or tongue 14 may be for example 5 to 20 mm. long, preferably 7 to 15 mm. long and in particular about 9 to 12 mm. long; it may be 2 to 7 mm. wide, more preferably 3 to 5 mm. wide, in particular about 3.5 to 4 mm. wide; and it may be about 2 to 4 times as long as it is wide, preferably about 2.5 to 3 times. In order to produce the desired "one-way" sounding effect as mentioned above, the reed or tongue 14 is preferably set towards container 5 at a small angle to the plane of the membrane 12. The angle may be for example about 2 to 4 degrees, preferably about 3 degrees; for a reed or tongue 9 to 12 mm. long, its free end should be about 0.5 mm. out of the plane of the membrane. If necessary, more than one reed or tongue 14, if desired tuned to different pitches, can be incorporated into the membrane 12.

The membrane 12 may be if necessary pigmented or metalplated on one surface so that the two surfaces have a different appearance; this provides a visual check that it has been inserted correctly.

The membrane 12 can be stamped out on a suitable machine, which can simultaneously set the reed or tongue 14 at the necessary angle for example by means of a slight protrusion on the punch. It can then be inserted into the inhalation device 1. If desired, the stamping machine can be designed to leave a plurality of flexible protruding pieces which, when the membrane is inserted into the inhalation device 1, bear against the sides of the skirt 2 and grip it and prevent the membrane 12 from falling out.

The sounding device 18 illustrated in FIGS. 3, 4, and 5 is moulded of plastic and is of such a size as to be readily inserted within the skirt 2. It consists of a membrane-like plate 21 and a flange 22. The plate 21 has a recess 23 with a tongue or reed 24 therein. Also in the plate 21 is a hole or plurality of holes 27 designed to provide an air passageway through the membrane 18. The number and size of these holes 27 are chosen to enable an asthmatic patient, especially a child, to inhale readily through the mouth-piece 4 of the inhalation device 1. Furthermore, these holes 27 provide a by-pass for the air flowing past the tongue or reed 24, which therefore does not give a clear note until the patient is inhaling sufficiently deeply.

The flange 22 has a number of grooves 28 therein designed to engage with corresponding ribs 15 in the skirt 2 of the inhalation device 1. Near the center of the membrane 18 is an aperture 25 designed to receive the boss 8. A rim 26 around aperture 25 and on the surface from which the flange 22 rises limits the protrusion of the boss 8 into the aperture 25.

The recess 23 in which the tongue or reed 24 is situated is defined on the other face of the plate 21 by abutments 29 serving to act as protection for the tongue or reed 24.

This plastic sounding device 18 can conveniently be made of polystyrene, and may for example be about 2 mm. thick throughout, except where the tongue or reed 24 is mounted. In this sounding device, the tongue or reed 24 can now be smaller and thinner than for the metal membrane described above, and yet still provide a good note: for example, it may be about 2 mm. by 11 mm. in size, and about 0.3 mm. to 0.5 mm. thick. The free end 30 of tongue or reed 24 is displaced slightly in the direction of the flange 22, i.e. against the air-current as described above for the metal membrane 12 and reed 14, in order to provide a similar one-way sounding means. The direction of air current that produces the sound is shown in FIGS. 4 and 5 by arrows 31.

This plastic sounding device 18 is easy to insert both mechanically and manually, since the flange 22 and grooves 28 guide it smoothly into the skirt 2. Once it is in place with the rim 26 abutting against the end of the boss 8, there is no tendency for it to slide out, since it is designed to fit snugly. The combination of the flange 22 and the grooves 28 allows for small variations in size of this type of membrane 18 without causing difficulties in insertion or letting it fall out easily.

The plastic sounding device 18 gives on inhalation a good steady note, which can if necessary be designed to be rather more discrete than that of the metal membrane described above, so that an asthmatic patient using it in a public place need not feel unduly embarrassed.

The mounting of the tongue or reed 24 in the recess 23 protects it from pressure during insertion and ensures that it will not be damaged by the flat end of an insertion tool, which will bear against the surface of the plate 21 or against the flange 22.

The number of holes 27 and their size depend upon the power of the patient's lungs; the particular needs of an individual patient will if necessary be evaluated by the attending physician. The requirements for most patients will lie within the range of one or two holes of diameter 2 to 4 mm., a narrow airway being particularly suitable for a child.

The plastic sounding device 18 can readily be manufactured by injection-moulding.

If desired, an inhalation device 1 containing a sounding device 12 or 18 such as described above can have an aperture in the back of the head-piece 3, which the patient can leave open if he wishes to use the inhalation device silently; if he wishes to use the sound to indicate when he should inhale, he can place his finger over this aperture.

In using the inhalation device 1, the patient inserts the container 5 into the skirt 2; he empties his lungs, puts the mouth-piece 4 into his mouth, grips it with his teeth and closes his lips. He then deeply inhales through the mouth, and presses the container 5 (to actuate it) when he hears the sound from the membrane. He continues inhaling for as long as possible after actuating the container, and then holds his breath as long as possible. The present inhalation device can also be used by a doctor in demonstrating to a patient the importance of synchronizing inhalation through the mouth and actuating the container, so that the patient can better use an unmodified device.

I claim:

1. An inhalation device of the type adapted to receive and locate an aerosol container designed to administer a multiplicity of metered doses, said aerosol container having a composition under pressure therein and having metering valve means including a valve stem and associated metering means, the valve stem having an axial discharge tube extending therethrough for discharge of a metered dose upon actuation of said metering valve means by depression of said valve stem, said inhalation device comprising a body having a skirt adapted to receive and locate said aerosol container in a first end thereof and a head-piece connected to a second end of said skirt, a mouth-piece extending from said head-piece and in communication therewith, and an audible signal generating means, said head-piece having actuating means for said metering valve means and a discharge passageway leading to a discharge orifice directed towards said mouth-piece, said actuating means being engageable with the valve stem upon locating of the container within the skirt and operable to actuate the metering valve means whereby a metered dose is discharged through the valve stem discharge tube and the discharge passageway and discharge orifice into the mouth-piece, an air-passageway extending through at least part of said body from a location at least upstream of said actuating means to said mouth-piece and providing a path for air to flow from the ambient into the mouth-piece upon inhalation through the mouth piece, wherein said audible signal generating means is located in said air-passageway within the body upstream of said discharge orifice and surrounds the actuating means for the metering valve means, and is actuatable upon inhalation through said mouth-piece when said inhalation device is in engagement with said container.

2. A device as claimed in claim 1 wherein said actuating means for said metering valve means comprises a valve stem boss adapted to receive the valve stem within a discharge passageway therein, said discharge passageway having means for limiting entry therein of said valve stem and a discharge orifice communicating with said discharge passageway and adapted to discharge said metered dose through said mouth-piece.

3. A device as claimed in claim 2 wherein said means generating an audible signal is located upstream of said boss between the space reserved for the container and said boss.

4. A device as claimed in claim 3 wherein said means generating an audible signal abuts against the valve stem boss, preferably against the end surface thereof facing the container.

5. A device as claimed in claim 4 wherein said means generating an audible signal is apertured to receive the end surface thereof and has a rim to limit penetration of said boss.

6. A device as claimed in claim 1 wherein said means generating an audible signal is responsive to an air-flow in one direction only past said means and out through said mouth-piece.

7. A device as claimed in claim 1 wherein the sound-generating part of said means generating an audible signal is a vibratory reed or tongue.

8. A device as claimed in claim 7 wherein said means generating an audible signal is a thin membrane having the vibratory reed or tongue therein.

9. A device as in claim 8 wherein said membrane is apertured to facilitate inhalation.

10. A device as claimed in claim 7 wherein said membrane has an upstanding supporting part.

11. A device as in claim 10 wherein said upstanding supporting part is a continuous flange which leans against said skirt.

12. An inhalation device comprising a body having a skirt adapted to locate an aerosol container on a first end thereof and a head-piece connected to a second end of said skirt, a mouth-piece extending from said head-piece and in communication therewith, and an audible signal generating means, said skirt being adapted to receive, locate and accomodate an aerosol container of the type having a composition under pressure therein and having metering valve means including a valve stem and associated metering means, the valve stem having an axial discharge tube extending therethrough for discharge of a metered dose upon actuation of said metering valve means by depression of said valve stem, said head-piece having a valve stem boss adapted to receive said valve stem with a discharge passageway therein, and said valve stem boss having means for limiting entry to said valve stem into said valve stem boss and a discharge orifice communicating with said discharge passageway and adapted to discharge said metered dose through said mouth-piece, said air path being defined in said skirt by channels provided between said skirt and the space reserved for the container, an air-passageway extending through at least part of said body from a location at least upstream of said boss to said mouth-piece and providing a path for air to flow from the ambient into the mouth-piece upon inhalation through the mouth-piece, wherein said audible signal generating means is a thin membrane located in said air path downstream of the container and abutting against said boss, and having a vibratory reed or tongue therein, said reed or tongue being bent toward the container so as to vibrate only when air flows inwardly through the skirt and outwardly through the mouth-piece.

13. A device as claimed in claim 12 in combination with an aerosol container.

14. A sounding device suitable for use in the inhalation device according to claim 12 wherein said signal generating means comprises a substantially planar membrane-like member adapted to block substantially the air-passageway of said inhalation device and bearing a vibratory tongue or reed substantially in the plane of the membrane-like member and having an aperture to receive the actuating means for the metering valve means or the valve stem of the container.

15. A sounding device as claimed in claim 14 wherein said membrane is apertured to facilitate breathing and has a continuous flange adapted to bear against the skirt for support.

* * * * *